(12) United States Patent
Hall et al.

(10) Patent No.: US 9,199,014 B2
(45) Date of Patent: Dec. 1, 2015

(54) WOUND MANAGEMENT

(75) Inventors: Kristian Hall, Hull (GB); Edward Yerbury Hartwell, York (GB)

(73) Assignee: Smith & Nephew PLC, London (GB)

( * ) Notice: Subject to any disclaimer, the term of this patent is extended or adjusted under 35 U.S.C. 154(b) by 242 days.

(21) Appl. No.: 12/746,502

(22) PCT Filed: Dec. 5, 2008

(86) PCT No.: PCT/GB2008/051159
§ 371 (c)(1),
(2), (4) Date: Sep. 21, 2010

(87) PCT Pub. No.: WO2009/071948
PCT Pub. Date: Jun. 11, 2009

(65) Prior Publication Data
US 2011/0028917 A1    Feb. 3, 2011

(30) Foreign Application Priority Data
Dec. 6, 2007 (GB) .................................. 0723875.1

(51) Int. Cl.
*A61M 1/00* (2006.01)
*A61M 3/02* (2006.01)

(52) U.S. Cl.
CPC ............. *A61M 1/0084* (2013.01); *A61M 1/007* (2014.02); *A61M 1/0058* (2013.01); *A61M 1/0068* (2014.02); *A61M 1/0088* (2013.01); *A61M 3/0262* (2013.01); *A61M 3/0279* (2013.01)

(58) Field of Classification Search
CPC ............ A61M 1/0058; A61M 1/0088; A61M 2001/0068; A61M 3/0262; A61M 1/0068; A61M 1/0084; A61M 1/007; A61M 1/0031; A61M 1/0062; A61M 1/0092; A61F 2013/00536; A61F 13/00068
USPC .......................................... 604/317–327, 354
See application file for complete search history.

(56) References Cited

U.S. PATENT DOCUMENTS 4,735,606 A * 4/1988 Davison ......................... 604/28
4,969,880 A 11/1990 Zamierowski
(Continued)

FOREIGN PATENT DOCUMENTS

GB        2307180      6/2000
WO     WO 01/37922    5/2001
(Continued)

OTHER PUBLICATIONS

European Second Office Action for European Application No. 08 856 265.7 dated Oct. 19, 2012.
(Continued)

*Primary Examiner* — Philip R Wiest
*Assistant Examiner* — Ariana Zimbouski
(74) *Attorney, Agent, or Firm* — Knobbe, Martens, Olson & Bear, LLP

(57) ABSTRACT

A method and apparatus are disclosed for delivering at least one agent to a wound site. The method includes the steps of providing a delivery tube having an outlet at a wound site, covering the wound site with a drape and introducing agent at an agent inlet port of the delivery tube. The agent passes along the delivery tube through the drape to the wound site. The agent can be a wide variety or mixture of fluids such as but not limited to pain relief medicament, anti-biotics, saline solution and/or hydrating fluid.

11 Claims, 12 Drawing Sheets

(56) References Cited

U.S. PATENT DOCUMENTS

| | | | |
|---|---|---|---|
| 5,527,293 | A | 6/1996 | Zamierowski |
| 5,636,643 | A | 6/1997 | Argenta et al. |
| 5,645,081 | A | 7/1997 | Argenta et al. |
| 6,142,982 | A | 11/2000 | Hunt et al. |
| 6,345,623 | B1 * | 2/2002 | Heaton et al. ........... 128/897 |
| 6,398,767 | B1 | 6/2002 | Fleischmann |
| 6,648,862 | B2 | 11/2003 | Watson |
| 6,685,681 | B2 | 2/2004 | Lockwood et al. |
| 6,752,794 | B2 | 6/2004 | Lockwood et al. |
| 6,936,037 | B2 | 8/2005 | Bubb et al. |
| 6,951,553 | B2 | 10/2005 | Bubb et al. |
| 6,979,324 | B2 * | 12/2005 | Bybordi et al. .......... 604/313 |
| 7,004,915 | B2 | 2/2006 | Boynton et al. |
| 7,108,683 | B2 | 9/2006 | Zamierowski |
| 7,195,624 | B2 | 3/2007 | Lockwood et al. |
| 7,198,046 | B1 | 4/2007 | Argenta et al. |
| 7,216,651 | B2 | 5/2007 | Argenta et al. |
| 7,381,859 | B2 | 6/2008 | Hunt et al. |
| 7,438,705 | B2 | 10/2008 | Karpowicz et al. |
| 7,524,315 | B2 | 4/2009 | Blott et al. |
| 7,534,240 | B1 | 5/2009 | Johnson |
| 7,615,036 | B2 | 11/2009 | Joshi et al. |
| 7,645,269 | B2 | 1/2010 | Zamierowski |
| 7,753,894 | B2 * | 7/2010 | Blott et al. ............ 604/305 |
| 7,759,538 | B2 | 7/2010 | Fleischmann |
| 7,779,625 | B2 | 8/2010 | Joshi et al. |
| 7,794,438 | B2 | 9/2010 | Henley et al. |
| 7,794,450 | B2 | 9/2010 | Blott et al. |
| 8,062,272 | B2 | 11/2011 | Weston |
| 2002/0082566 | A1 | 6/2002 | Stenzler |
| 2005/0085795 | A1 * | 4/2005 | Lockwood et al. ....... 604/543 |
| 2005/0197626 | A1 * | 9/2005 | Moberg et al. .......... 604/131 |
| 2005/0267424 | A1 * | 12/2005 | Eriksson et al. ......... 604/304 |
| 2006/0100594 | A1 * | 5/2006 | Adams et al. ........... 604/313 |
| 2007/0141128 | A1 | 6/2007 | Blott et al. |
| 2007/0219588 | A1 * | 9/2007 | Freeman ................ 607/5 |
| 2008/0215019 | A1 * | 9/2008 | Malamutmann .......... 604/305 |
| 2010/0262094 | A1 * | 10/2010 | Walton et al. .......... 604/319 |
| 2010/0262095 | A1 | 10/2010 | Hall |
| 2011/0172615 | A2 | 7/2011 | Greener |

FOREIGN PATENT DOCUMENTS

| | | | |
|---|---|---|---|
| WO | WO 03/073970 | | 9/2003 |
| WO | WO 2004/037334 | | 5/2004 |
| WO | WO 2005/046760 | | 5/2005 |
| WO | WO 2005/046761 | | 5/2005 |
| WO | WO 2005/046762 | | 5/2005 |
| WO | WO 2005/105180 | | 11/2005 |
| WO | WO 2005/115523 | | 12/2005 |
| WO | WO 2006/056408 | * | 6/2006 |
| WO | WO 2006/114638 | * | 11/2006 ............ A61M 1/00 |
| WO | WO 2007/062024 | | 5/2007 |

OTHER PUBLICATIONS

Bevan, Damon, et al.: "Diverse and potent activities of HGF/SF in skin wound repair", Journal of Pathology, J Pathol 2004; 203: 831-838.

Mitchell, Richard N., et al.: "Role of Stem Cells in Tissue Homeostasis", Pocket Companion to Robbins and Cotran Pathologic Basis of Disease, 7th Ed., 2006.

International Search Report for PCT/GB2008/051159, mailed Apr. 16, 2009.

* cited by examiner

WOUND MANAGEMENT

CROSS-REFERENCE TO RELATED APPLICATIONS

This application is a U.S. National Phase of the PCT International Application No. PCT/GB2008/051159 filed on Dec. 5, 2008, designating the United States and published on Jun. 11, 2009 as WO 2009/071948, which claims priority to Great Britain Patent Application No. 0723875.1, filed on Dec. 6, 2007. The disclosure of both prior applications is incorporated by reference in their entirety and should be considered a part of this specification.

BACKGROUND OF THE INVENTION

Field of the Invention

The present invention relates to apparatus and a method for the application of topical negative pressure (TNP) therapy to wounds. In particular, but not exclusively, the present invention relates to a method and apparatus for delivering an agent such as medicament or hydrating fluid through or under a drape covering a wound site.

There is much prior art available relating to the provision of apparatus and methods of use thereof for the application of TNP therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In our co-pending International patent application, WO 2004/037334, apparatus, a wound dressing and a method for aspirating, irrigating and cleansing wounds are described. In very general terms, this invention describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In our co-pending International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound. In our co-pending International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above references is included herein by reference.

However, the above apparatus and methods are generally only applicable to a patient when hospitalised as the apparatus is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus.

GB-A-2 307 180 describes a portable TNP therapy unit which may be carried by a patient clipped to belt or harness. It will be appreciated however that there are limitations as to how parameters associated with a wound site can be maintained.

In general it is known that the bacterial load of wounds can increase over time and that wounds can also dry out whilst under negative pressure wound therapy. This is particularly so when using conventional wound dressings such as ALLEVYN (trademark). At present a way of reducing wound/tissue infection is by regularly changing dressings which are located over a wound site. This has an impact on the patient since changing dressing can lead to patient discomfort, increased cost associated with the replacement dressings themselves and can increase the chances of patient to patient infection.

It is also known that from time to time it is advantageous to deliver one or more agents such as pain relief medicament, anti-biotics, wound irrigation etc to a wound site. With known techniques a dressing or drape kept over the wound site to prevent infection must be removed prior to delivery of the agent with a new drape/dressing being required subsequent to introduction of the agent. Again this can lead to patient discomfort, increases costs and increases likelihood of cross infection.

U.S. Pat. No. 6,398,767 and WO03/073970 each show how substances can be introduced at a wound site but the techniques shown are complicated, can be prone to fault and disclose use of only a limited number of agents.

Summary of Some Exemplifying Embodiments

It is an aim of the present invention to at least partly mitigate the above-mentioned problems.

It is an aim of embodiments of the present invention to provide a method and apparatus which permits one or more agents such as painkillers, anti-biotics and/or wound irrigation to be introduced at a wound site without having to remove/replace a drape/dressing covering the wound site.

It is an aim of embodiments of the present invention to provide a method and apparatus which is able to automatically deliver agent continuously or at predetermined time intervals to a wound site.

It is an aim of embodiments of the present invention to provide a method and apparatus which permits a user to quickly and efficiently deliver a highly precise dose of medicament or other such agent to a wound site.

According to a first aspect of the present invention there is provided a method of delivering at least one agent to a wound site; comprising the steps of:

providing a delivery tube having an outlet at a wound site; covering the wound site with a drape; and
introducing agent at an agent inlet port of the delivery tube, agent passing along the delivery tube through or under the drape to the wound site.

The invention is comprised in part of an overall apparatus for the provision of TNP therapy to a patient in almost any environment. The apparatus is lightweight, may be mains or battery powered by a rechargeable battery pack contained within a device (henceforth, the term "device" is used to connote a unit which may contain all of the control, power supply, power supply recharging, electronic indicator means and means for initiating and sustaining aspiration functions to a wound and any further necessary functions of a similar nature). When outside the home, for example, the apparatus may provide for an extended period of operation on battery power and in the home, for example, the device may be connected to the mains by a charger unit whilst still being used and operated by the patient.

The overall apparatus of which the present invention is a part comprises: a dressing covering the wound and sealing at least an open end of an aspiration conduit to a cavity formed over the wound by the dressing; an aspiration tube comprising at least one lumen therethrough leading from the wound dressing to a waste material canister for collecting and holding wound exudates/waste material prior to disposal; and, a power, control and aspiration initiating and sustaining device associated with the waste canister.

The dressing covering the wound may be any type of dressing normally employed with TNP therapy and, in very general terms, may comprise, for example, a semi-permeable, flexible, self-adhesive drape material, as is known in the dressings art, to cover the wound and seal with surrounding sound tissue to create a sealed cavity or void over the wound. There may aptly be a porous barrier and support member in the cavity between the wound bed and the covering material to enable an even vacuum distribution to be achieved over the area of the wound. The porous barrier and support member being, for example, a gauze, a foam, an inflatable bag or known wound contact type material resistant to crushing under the levels of vacuum created and which permits transfer of wound exudates across the wound area to the aspiration conduit sealed to the flexible cover drape over the wound.

The aspiration conduit may be a plain flexible tube, for example, having a single lumen therethrough and made from a plastics material compatible with raw tissue, for example. However, the aspiration conduit may have a plurality of lumens therethrough to achieve specific objectives relating to the invention. A portion of the tube sited within the sealed cavity over the wound may have a structure to enable continued aspiration and evacuation of wound exudates without becoming constricted or blocked even at the higher levels of the negative pressure range envisaged.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

The aspiration conduit at its distal end remote from the dressing may be attached to the waste canister at an inlet port or connector. The device containing the means for initiating and sustaining aspiration of the wound/dressing may be situated between the dressing and waste canister, however, in a preferred embodiment of the apparatus embodying the present invention, the device may aspirate the wound/dressing via the canister thus, the waste canister may preferably be sited between the wound/dressing and device.

The aspiration conduit at the waste material canister end may preferably be bonded to the waste canister to prevent inadvertent detachment when being caught on an obstruction, for example.

The canister may be a plastics material moulding or a composite unit comprising a plurality of separate moldings. The canister may aptly be translucent or transparent in order to visually determine the extent of filling with exudates. However, the canister and device may in some embodiments provide automatic warning of imminent canister full condition and may also provide means for cessation of aspiration when the canister reaches the full condition.

The canister may be provided with filters to prevent the exhaust of liquids and odours therefrom and also to prevent the expulsion of bacteria into the atmosphere. Such filters may comprise a plurality of filters in series. Examples of suitable filters may comprise hydrophobic filters of 0.2 µm pore size, for example, in respect of sealing the canister against bacteria expulsion and 1 µm against liquid expulsion.

Aptly, the filters may be sited at an upper portion of the waste canister in normal use, that is when the apparatus is being used or carried by a patient the filters are in an upper position and separated from the exudate liquid in the waste canister by gravity. Furthermore, such an orientation keeps the waste canister outlet or exhaust exit port remote from the exudate surface.

Aptly the waste canister may be filled with an absorbent gel such as ISOLYSEL (trade mark), for example, as an added safeguard against leakage of the canister when full and being changed and disposed of. Added advantages of a gel matrix within the exudate storing volume of the waste canister are that it prevents excessive movement, such as slopping, of the liquid, minimises bacterial growth and minimises odours.

The waste canister may also be provided with suitable means to prevent leakage thereof both when detached from the device unit and also when the aspiration conduit is detached from the wound site/dressing.

The canister may have suitable means to prevent emptying by a user (without tools or damage to the canister) such that a full or otherwise end-of-life canister may only be disposed of with waste fluid still contained.

The device and waste canister may have mutually complementary means for connecting a device unit to a waste canister whereby the aspiration means in the device unit automatically connects to an evacuation port on the waste canister such that there is a continuous aspiration path from the wound site/dressing to an exhaust port on the device.

Aptly, the exhaust port from the fluid path through the apparatus is provided with filter means to prevent offensive odours from being ejected into the atmosphere.

In general terms the device unit comprises an aspirant pump; means for monitoring pressure applied by the aspirant pump; a flowmeter to monitor fluid flow through the aspirant pump; a control system which controls the aspirant pump in response to signals from sensors such as the pressure monitoring means and the flowmeter, for example, and which control system also controls a power management system with regard to an on-board battery pack and the charging thereof and lastly a user interface system whereby various functions of the device such as pressure level set point, for example, may be adjusted (including stopping and starting of the apparatus) by a user.

The device unit may contain all of the above features within a single unified casing.

In view of the fact that the device unit contains the majority of the intrinsic equipment cost therein ideally it will also be able to survive impact, tolerate cleaning in order to be reusable by other patients.

In terms of pressure capability the aspiration means may be able to apply a maximum pressure drop of at least −200 mmHg to a wound site/dressing. The apparatus is capable of maintaining a predetermined negative pressure even under conditions where there is a small leak of air into the system and a high exudate flow.

The pressure control system may prevent the minimum pressure achieved from exceeding for example −200 mmHg so as not to cause undue patient discomfort. The pressure required may be set by the user at a number of discreet levels such as −50, −75, −100, −125, −150, −175 mmHg, for example, depending upon the needs of the wound in question and the advice of a clinician. Thus suitable pressure ranges in use may be from −25 to −80 mmHg, or −50 to −76 mmHg, or −50 to −75 mmHg as examples. The control system may also advantageously be able to maintain the set pressure within a tolerance band of +/−10 mmHg of the set point for 95% of the time the apparatus is operating given that leakage and exudation rates are within expected or normal levels.

Aptly, the control system may trigger alarm means such as a flashing light, buzzer or any other suitable means when various abnormal conditions apply such as, for example: pressure outside set value by a large amount due to a gross leak of air into system; duty on the aspiration pump too high due to a relatively smaller leakage of air into the system; pressure differential between wound site and pump is too high due, for example, to a blockage or waste canister full.

The apparatus of the present invention may be provided with a carry case and suitable support means such as a shoulder strap or harness, for example. The carry case may be adapted to conform to the shape of the apparatus comprised in the joined together device and waste canister. In particular, the carry case may be provided with a bottom opening flap to permit the waste canister to be changed without complete removal of the apparatus form the carry case.

The carry case may be provided with an aperture covered by a displaceable flap to enable user access to a keypad for varying the therapy applied by the apparatus. According to a second aspect of the present invention, there is provided apparatus for delivering at least one agent to a wound site, comprising:
 a drape for covering a wound site; and
 a substantially T-shaped delivery tube comprising an outlet, an agent inlet
port and an air inlet port.

BRIEF DESCRIPTION OF THE DRAWINGS

In order that the present invention may be more fully understood, examples will now be described by way of illustration only with reference to the accompanying drawings, of which.

DETAILED DESCRIPTION OF SOME EXEMPLIFYING EMBODIMENTS

Figure 1:
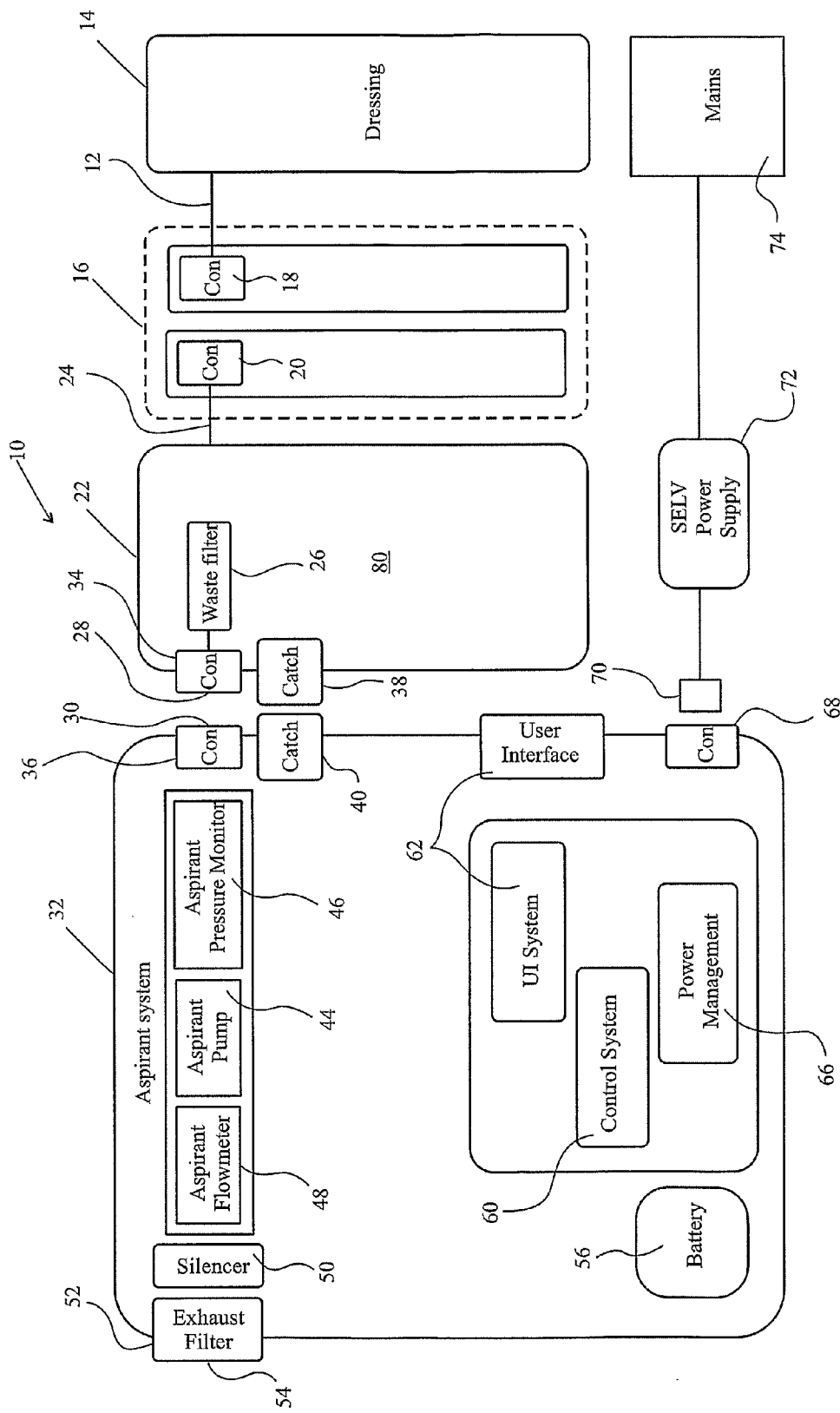
FIG. 1 shows a generalised schematic block diagram showing a general view of an apparatus and the constituent apparatus features thereof.

Referring now to FIGS. 1 to 4 of the drawings and where the same or similar features are denoted by common reference numerals.

FIG. 1 shows a generalised schematic view of an apparatus 10 of a portable topical negative pressure (TNP) system. It will be understood that embodiments of the present invention are generally applicable to use in such a TNP system. Briefly, negative pressure wound therapy assists in the closure and healing of many forms of "hard to heal" wounds by reducing tissue oedema; encouraging blood flow and granular tissue formation; removing excess exudate and may reduce bacterial load (and, therefore, infection). In addition the therapy allows for less disturbance of a wound leading to more rapid healing. The TNP system is detailed further hereinafter but in summary includes a portable body including a canister and a device with the device capable of providing an extended period of continuous therapy within at least a one year life span. The system is connected to a patient via a length of tubing with an end of the tubing operably secured to a wound dressing on the patient.

More particularly, as shown in FIG. 1, the apparatus comprises an aspiration conduit 12 operably and an outer surface thereof at one end sealingly attached to a dressing 14. The dressing 14 will not be further described here other than to say that it is formed in a known manner from well know materials to those skilled in the dressings art to create a sealed cavity over and around a wound to be treated by TNP therapy with the apparatus of the present invention. The aspiration conduit has an in-line connector 16 comprising connector portions 18, 20 intermediate its length between the dressing 14 and a waste canister 22. The aspiration conduit between the connector portion 20 and the canister 22 is denoted by a different reference numeral 24 although the fluid path through conduit portions 12 and 24 to the waste canister is continuous. The connector portions 18, 20 join conduit portions 12, 24 in a leak-free but disconnectable manner. The waste canister 22 is provided with filters 26 which prevent the escape via an exit port 28 of liquid and bacteria from the waste canister. The filters may comprise a 1 µm hydrophobic liquid filter and a 0.2 µm bacteria filter such that all liquid and bacteria is confined to an interior waste collecting volume of the waste canister 22. The exit port 28 of the waste canister 22 mates with an entry/suction port 30 of a device unit 32 by means of mutually sealing connector portions 34, 36 which engage and seal together automatically when the waste canister 22 is attached to the device unit 32, the waste canister 22 and device unit 32 being held together by catch assemblies 38, 40. The device unit 32 comprises an aspirant pump 44, an aspirant pressure monitor 46 and an aspirant flowmeter 48 operably connected together. The aspiration path takes the aspirated fluid which in the case of fluid on the exit side of exit port 28 is gaseous through a silencer system 50 and a final filter 52 having an activated charcoal matrix which ensures that no odours escape with the gas exhausted from the device 32 via an exhaust port 54. The filter 52 material also serves as noise reducing material to enhance the effect of the silencer system 50. The device 32 also contains a battery pack 56 to power the apparatus which battery pack also powers the control system 60 which controls a user interface system 62 controlled via a keypad (not shown) and the aspiration pump 44 via signals from sensors 46, 48. A power management system 66 is also provided which controls power from the battery pack 56, the recharging thereof and the power requirements of the aspirant pump 44 and other electrically operated components. An electrical connector 68 is provided to receive a power input jack 70 from a SELV power supply 72 connected to a mains supply 74 when the user of the apparatus or the apparatus itself is adjacent a convenient mains power socket.

Figure 2:
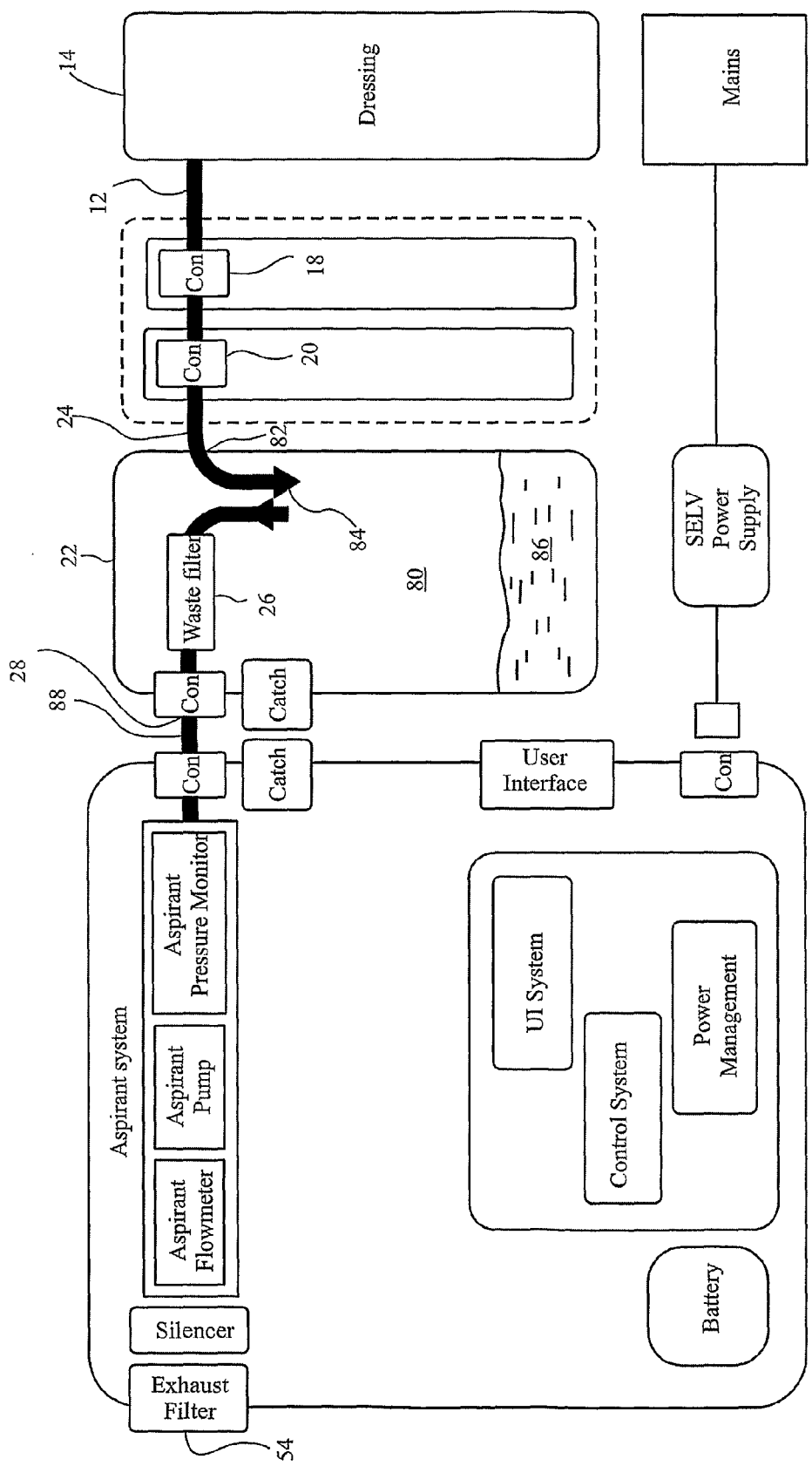
FIG. 2 shows a similar generalised schematic block diagram to FIG. 1 and showing fluid paths therein.

FIG. 2 shows a similar schematic representation to FIG. 1 but shows the fluid paths in more detail. The wound exudate is aspirated from the wound site/dressing 14 via the conduit 12, the two connector portions 18, 20 and the conduit 24 into the waste canister 22. The waste canister 22 comprises a relatively large volume 80 in the region of 500 ml into which exudate from the wound is drawn by the aspiration system at an entry port 82. The fluid 84 drawn into the canister volume 80 is a mixture of both air drawn into the dressing 14 via the semi-permeable adhesive sealing drape (not shown) and liquid 86 in the form of wound exudates. The volume 80 within the canister is also at a lowered pressure and the gaseous element 88 of the aspirated fluids is exhausted from the canister volume 80 via the filters 26 and the waste canister exhaust exit port 28 as bacteria-free gas. From the exit port 28 of the waste canister to the final exhaust port 54 the fluid is gaseous only.

Figure 3:
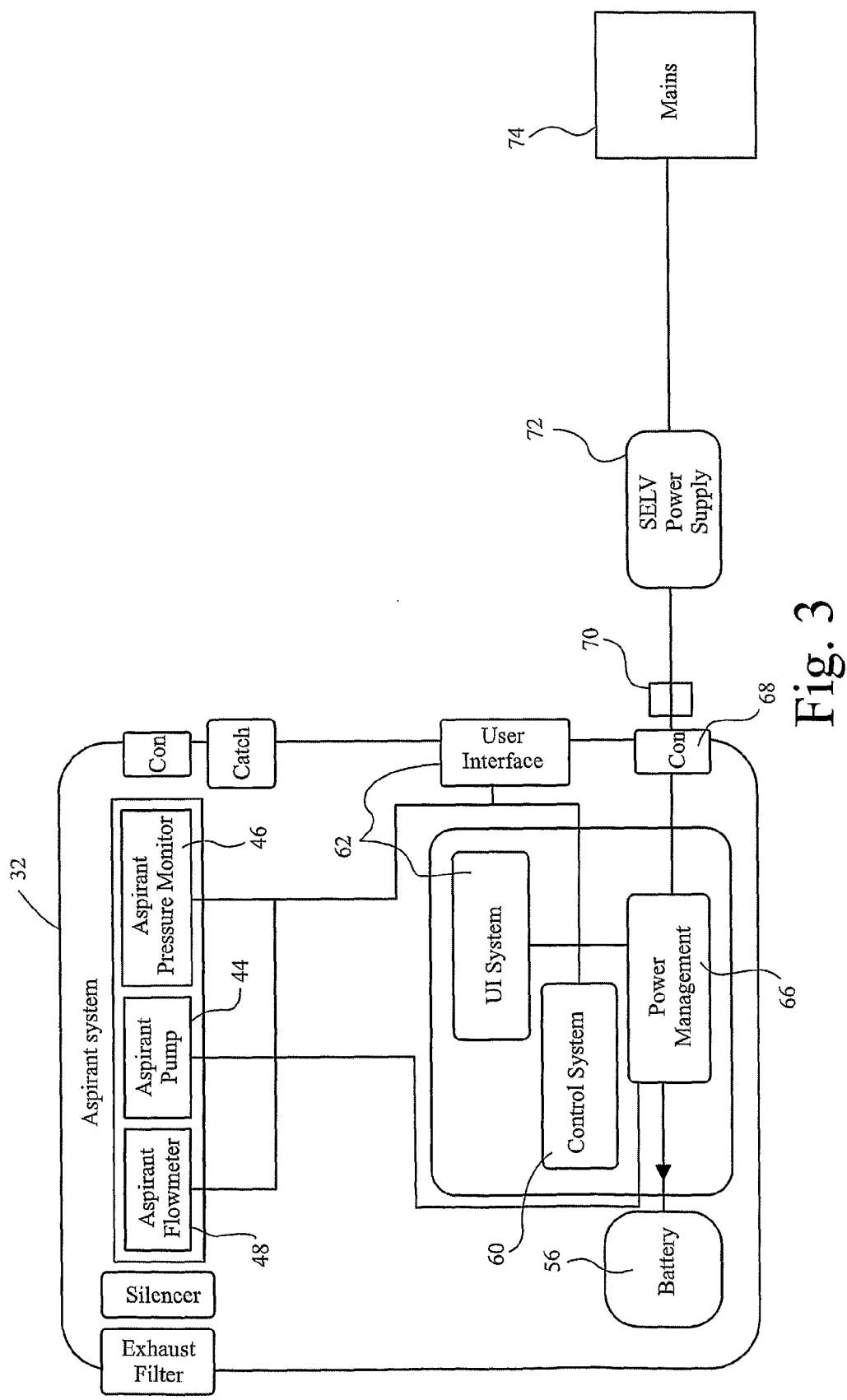
FIG. 3 shows a generalised schematic block diagram similar to FIG. 1 but of a device unit only and showing power paths for the various power consuming/producing features of the apparatus.

FIG. 3 shows a schematic diagram showing only the device portion of the apparatus and the power paths in the device of the apparatus embodying the present invention. Power is provided mainly by the battery pack 56 when the user is outside their home or workplace, for example, however, power may also be provided by an external mains 74 supplied charging unit 72 which when connected to the device 32 by the socket 68 is capable of both operating the device and recharging the battery pack 56 simultaneously. The power management system 66 is included so as to be able to control power of the TNP system. The TNP system is a rechargeable, battery powered system but is capable of being run directly from mains electricity as will be described hereinafter more fully with respect to the further figures. If disconnected from the mains the battery has enough stored charge for approximately 8 hours of use in normal conditions. It will be appreciated that batteries having other associated life times between recharge can be utilised. For example batteries providing less than 8 hours or greater than 8 hours can be used. When connected to the mains the device will run off the mains power and will simultaneously recharge the battery if depleted from portable use. The exact rate of battery recharge will depend on the load on the TNP system. For example, if the wound is very large or there is a significant leak, battery recharge will take longer than if the wound is small and well sealed.

Figure 4:
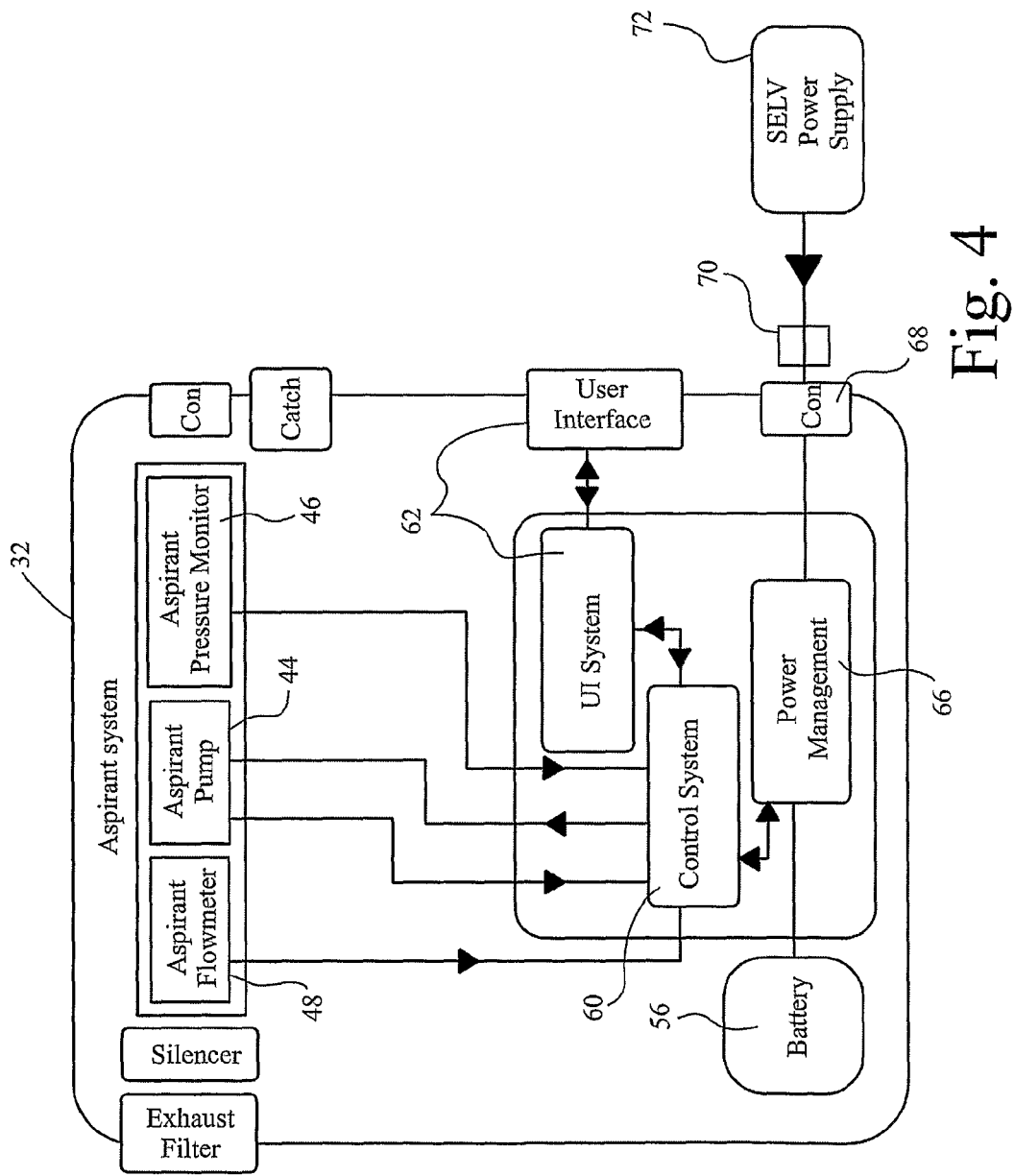
FIG. 4 shows a similar generalised schematic block diagram to FIG. 3 of the device unit and showing control system data paths for controlling the various functions and components of the apparatus.
Figure 5:
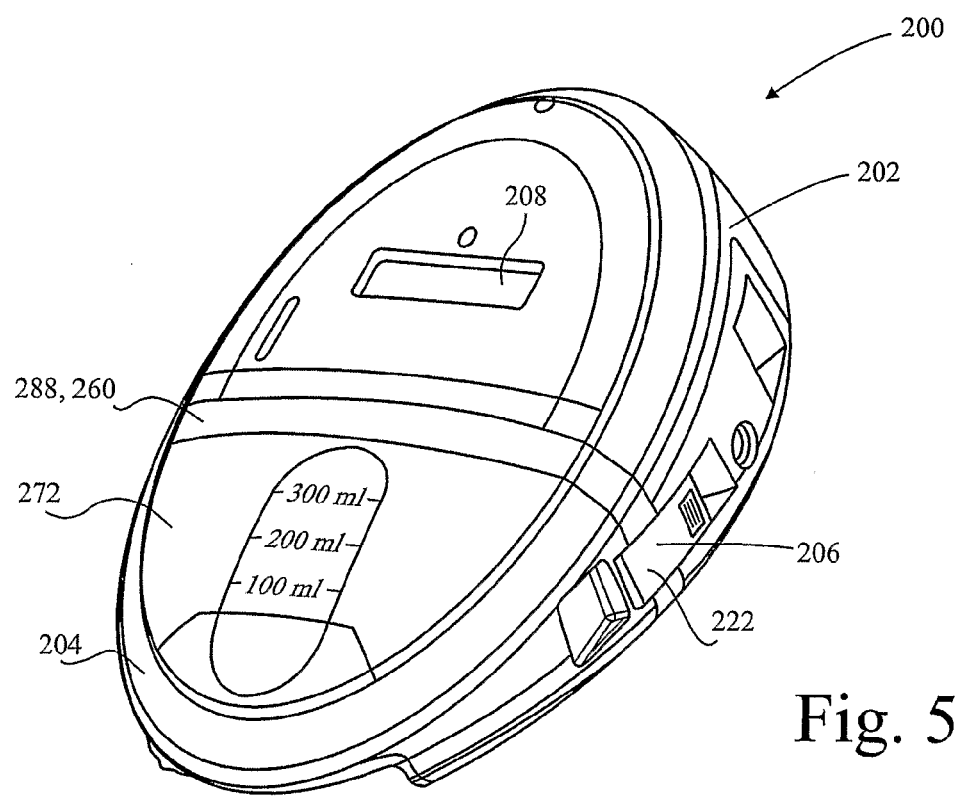
FIG. 5 shows a perspective view of an apparatus.
Figure 6:
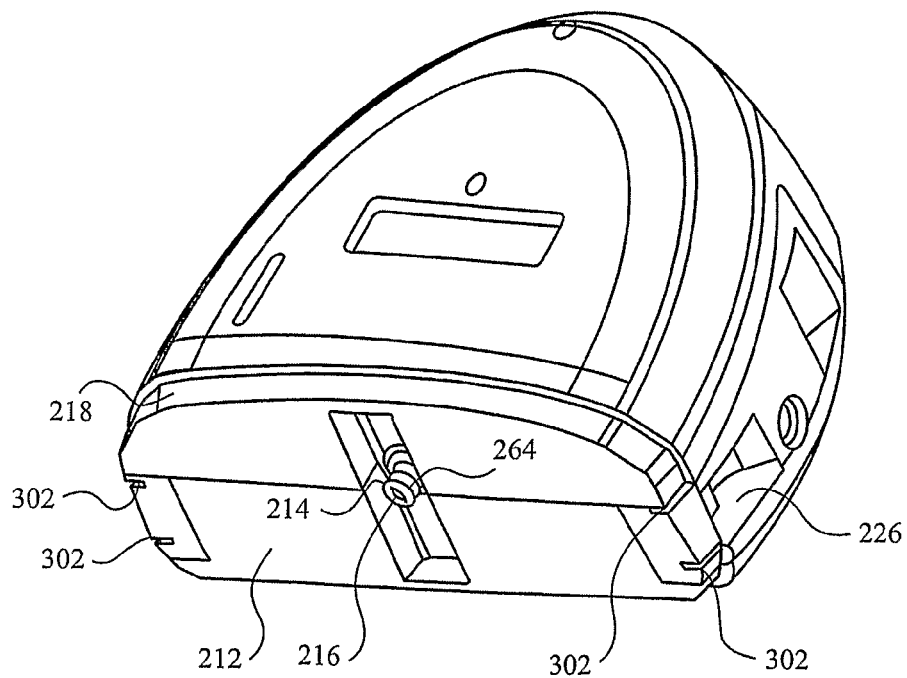
FIG. 6 shows a perspective view of an assembled device unit of the apparatus of FIG. 5.
Figure 7:
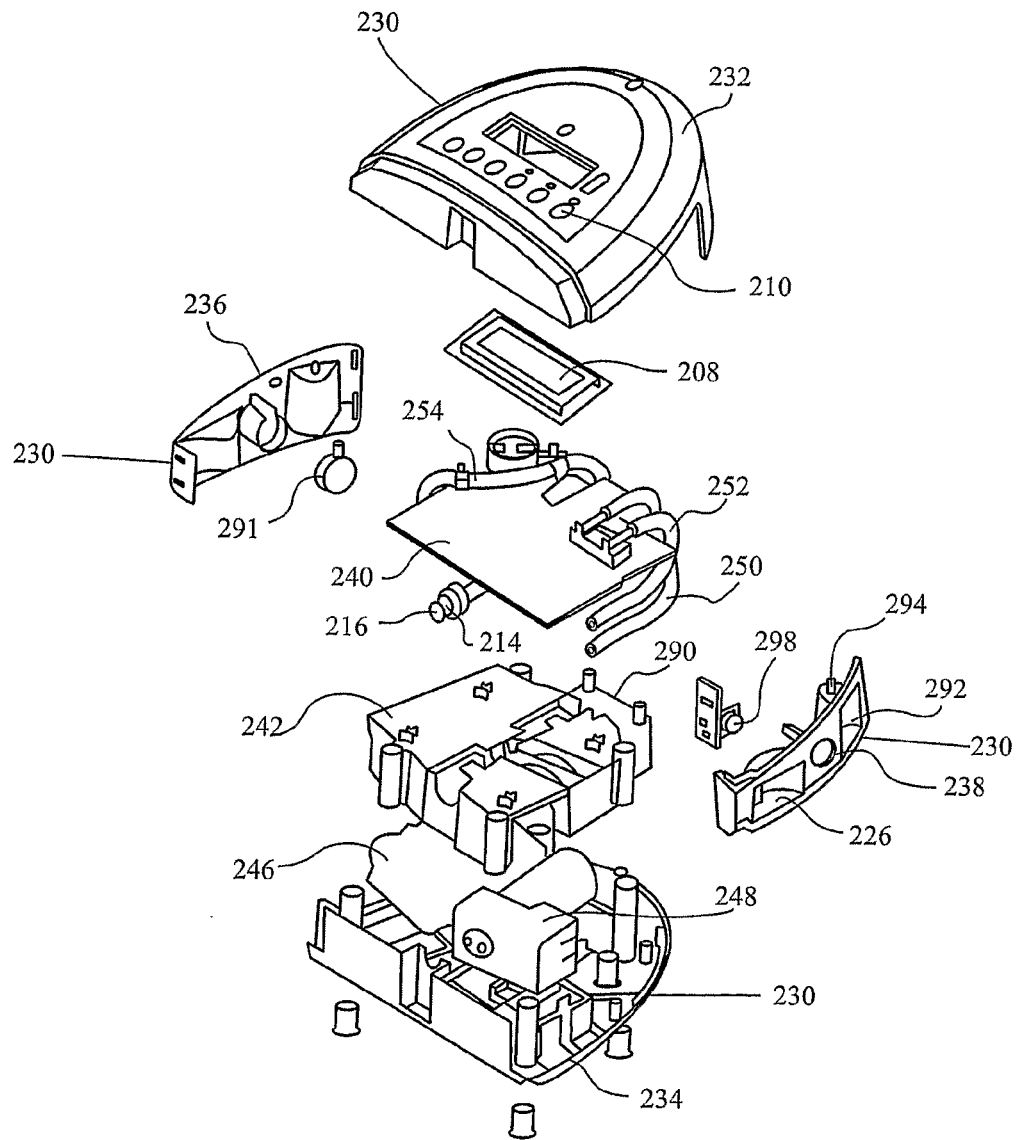
FIG. 7 shows an exploded view of the device unit of FIG. 6.

FIG. 4 shows the device 32 part of the apparatus embodying the present invention and the data paths employed in the control system for control of the aspirant pump and other features of the apparatus. A key purpose of the TNP system is to apply negative pressure wound therapy. This is accomplished via the pressure control system which includes the pump and a pump control system. The pump applies negative pressure; the pressure control system gives feedback on the pressure at the pump head to the control system; the pump control varies the pump speed based on the difference between the target pressure and the actual pressure at the pump head. In order to improve accuracy of pump speed and hence provide smoother and more accurate application of the negative pressure at a wound site, the pump is controlled by an auxiliary control system. The pump is from time to time allowed to "free-wheel" during its duty cycle by turning off the voltage applied to it. The spinning motor causes a "back electro-motive force" or BEMF to be generated. This BEMF can be monitored and can be used to provide an accurate measure of pump speed. The speed can thus be adjusted more accurately than can prior art pump systems.

According to embodiments of the present invention, actual pressure at a wound site is not measured but the difference between a measured pressure (at the pump) and the wound pressure is minimised by the use of large filters and large bore tubes wherever practical. If the pressure control measures that the pressure at the pump head is greater than a target pressure (closer to atmospheric pressure) for a period of time, the device sends an alarm and displays a message alerting the user to a potential problem such as a leak.

In addition to pressure control a separate flow control system can be provided. A flow meter may be positioned after the pump and is used to detect when a canister is full or the tube has become blocked. If the flow falls below a certain threshold, the device sounds an alarm and displays a message alerting a user to the potential blockage or full canister.

Figure 8:
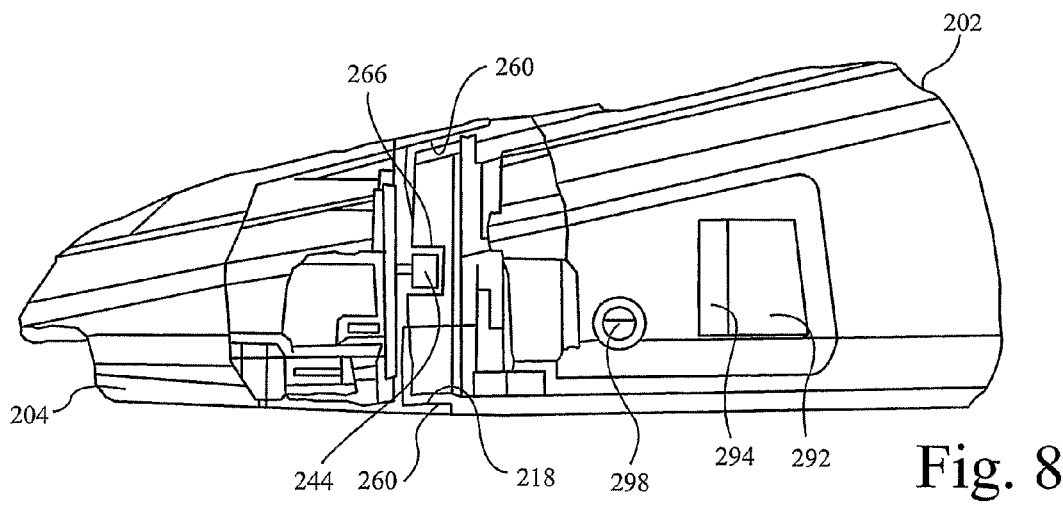
FIG. 8 shows a partially sectioned side elevation view through the interface between a waste canister and device unit of the apparatus.
Figure 9:
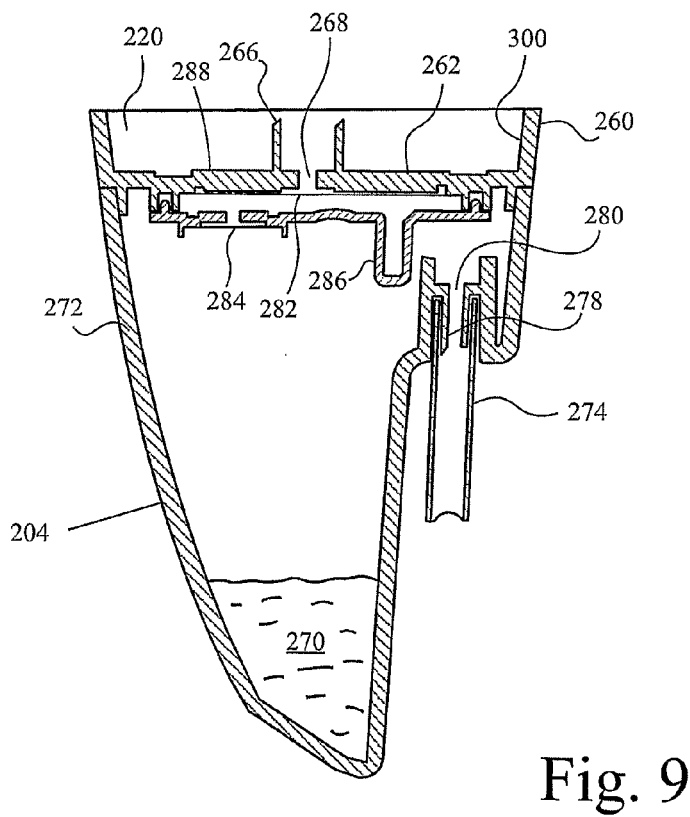
FIG. 9 shows a cross section through a waste canister of the apparatus of FIGS. 5 to 8.

Referring now to FIGS. 5 to 9 which show various views and cross sections of a preferred embodiment of apparatus 200 embodying the present invention. The preferred embodiment is of generally oval shape in plan and comprises a device unit 202 and a waste canister 204 connected together by catch arrangements 206. The device unit 202 has a liquid crystal display (LCD) 208, which gives text based feedback on the wound therapy being applied, and a membrane keypad 210, the LCD being visible through the membrane of the keypad to enable a user to adjust or set the therapy to be applied to the wound (not shown). The device has a lower, generally transverse face 212 in the centre of which is a spigot 214 which forms the suction/entry port 216 to which the aspiration means (to be described below) are connected within the device unit. The lower edge of the device unit is provided with a rebated peripheral male mating face 218 which engages with a co-operating peripheral female formation 220 on an upper edge of the waste canister 204 (see FIGS. 8 and 9). On each side of the device 202, clips 222 hinged to the canister 204 have an engaging finger (not shown) which co-operates with formations in recesses 226 in the body of the device unit. From FIG. 7 it may be seen that the casing 230 of the device unit is of largely "clamshell" construction comprising front and back mouldings 232, 234, respectively and left-hand and right-hand side inserts 236, 238. Inside the casing 230 is a central chassis 240 which is fastened to an internal moulded structural member 242 and which chassis acts as a mounting for the electrical circuitry and components and also retains the battery pack 246 and aspiration pump unit 248. Various tubing items 250, 252, 254 connect the pump unit 248 and suction/entry port 216 to a final gaseous exhaust via a filter 290. FIG. 8 shows a partially sectioned side elevation of the apparatus 200, the partial section being around the junction between the device unit 202 and the waste canister 204, a cross section of which is shown at FIG. 9. Theses views show the rebated edge 218 of the male formation on the device unit co-operating with the female portion 220 defined by an upstanding flange 260 around the top face 262 of the waste canister 204. When the waste canister is joined to the device unit, the spigot 214 which has an "O" ring seal 264 therearound sealingly engages with a cylindrical tube portion 266 formed around an exhaust/exit port 268 in the waste canister. The spigot 214 of the device is not rigidly fixed to the device casing but is allowed to "float" or move in its location features in the casing to permit the spigot 214 and seal 264 to move to form the best seal with the bore of the cylindrical tube portion 266 on connection of the waste canister to the device unit. The waste canister 204 in FIG. 9 is shown in an upright orientation much as it would be when worn by a user. Thus, any exudate 270 would be in the bottom of the internal volume of waste receptacle portion 272. An aspiration conduit 274 is permanently affixed to an entry port spigot 278 defining an entry port 280 to receive fluid aspirated from a wound (not shown) via the conduit 274. Filter members 282 comprising a 0.2 μm filter and 284 comprising a 1 μm filter are located by a filter retainer moulding 286 adjacent a top closure member or bulkhead 288 the filter members preventing any liquid or bacteria from being drawn out of the exhaust exit port 268 into the pump and aspiration path through to an exhaust and filter unit 290 which is connected to a casing outlet moulding at 291 via an exhaust tube (not shown) in casing side piece 236. The side pieces 236, 238 are provided with recesses 292 having support pins 294 therein to locate a carrying strap (not shown) for use by the patient. The side pieces 230 and canister 204 are also provided with features which prevent the canister and device from exhibiting a mutual "wobble" when connected together. Ribs (not shown) extending between the canister top closure member 288 and the inner face 300 of the upstanding flange 260 locate in grooves 302 in the device sidewalls when canister and device are connected. The casing 230 also houses all of the electrical equipment and control and power management features, the functioning of which was described briefly with respect to FIGS. 3 and 4 hereinabove. The side piece 238 is provided with a socket member 298 to receive a charging jack from an external mains powered battery charger (both not shown).

Figure 10:
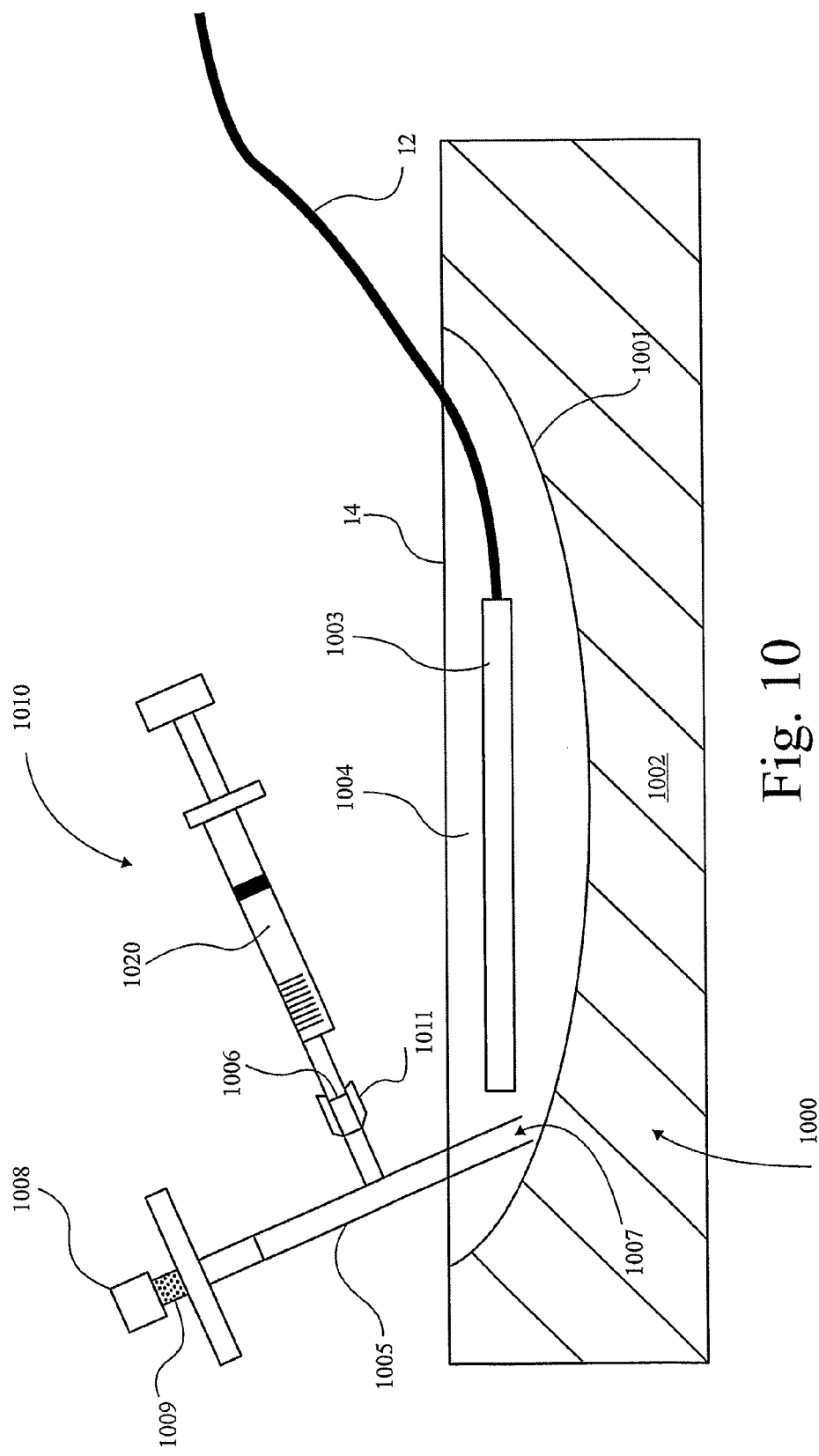
FIG. 10 illustrates a wound site.

It will be appreciated that the bacterial load of wounds can increase over time and that wounds can, unless evasive action is taken, dry out whilst under negative pressure wound therapy (NPWT). This is so when using conventional wound dressings. FIG. 10 illustrates a way in which bacterial load of a wound can be reduced or removed according to embodiments of the present invention. It will be appreciated that embodiments of the present invention can also be utilised to prevent wounds drying out and/or relieve localised pain and/or introduce anti-biotics and/or provide wound irrigation at a wound site.

As illustrated in FIG. 10 a wound site 1000 includes a wound bed 1001 in a skin layer 1002 of a patient. A drain 1003 is secured to a distal end of the aspiration conduit 12 via a connector. The drain is sealed to the dressing such that a reduced pressure can be maintained at the wound using a drape or other such sealing means. A gauze 1004 or other filler mechanism may be used in the wound site to pad out the area under the drape 14.

A generally T-shaped delivery tube 1005 extends through the drape 14. The projection of the delivery tube through the drape can be achieved either by providing a dressing with an inlet port (not shown) sized to accommodate the delivery tube diameter or by pinching the drape 14 around the delivery tube during dressing of the wound site. The delivery tube 1005 includes an agent inlet port 1006 through which agent can be introduced.

It will be appreciated that embodiments of the present invention can be used to deliver a wide variety of agents to the wound site. For example, but not exclusively, embodiments of the present invention can deliver powdered or fluid medicament and/or pain relief medicament and/or anti-biotics and/or saline solution and/or hydrating fluid and/or biologically active agents and/or growth factors and/or enzymes and/or anti inflammatories. Embodiments of the present invention can also be utilised to introduce a mixture of agents. When the agent is introduced at the inlet valve 1006 it passes along the delivery tube through the drape to the wound site, entering the wound site through an outlet 1007.

The delivery tube 1005 is also provided with a removable cap 1008 which can be resealably sealed on the end of the delivery tube. When an agent is to be introduced to the wound site the cap 1008 is removed to reveal a filter 1009 which is provided to allow air to fill the wound as desired. The air allows the injection port to be flushed and helps the removal of large volumes of fluid from the wound.

As illustrated in FIG. 10 agent can be introduced to the wound site using a syringe 1010 which contains a predetermined quantity of the agent to be introduced. The syringe is placed onto the side tube of the delivery tube with the required solution and then a pinch clamp 1011 or other such inlet valve is released. The cap 1008 is removed and fluid or dry agent then injected into the wound. When a predetermined quantity of the agent has been introduced the cap may be replaced back on the filter and the pinch clamp reapplied. The syringe may then be removed. NPWT can then be applied to the wound. Alternatively the NPWT may continue whilst the agent is introduced.

Figure 11:
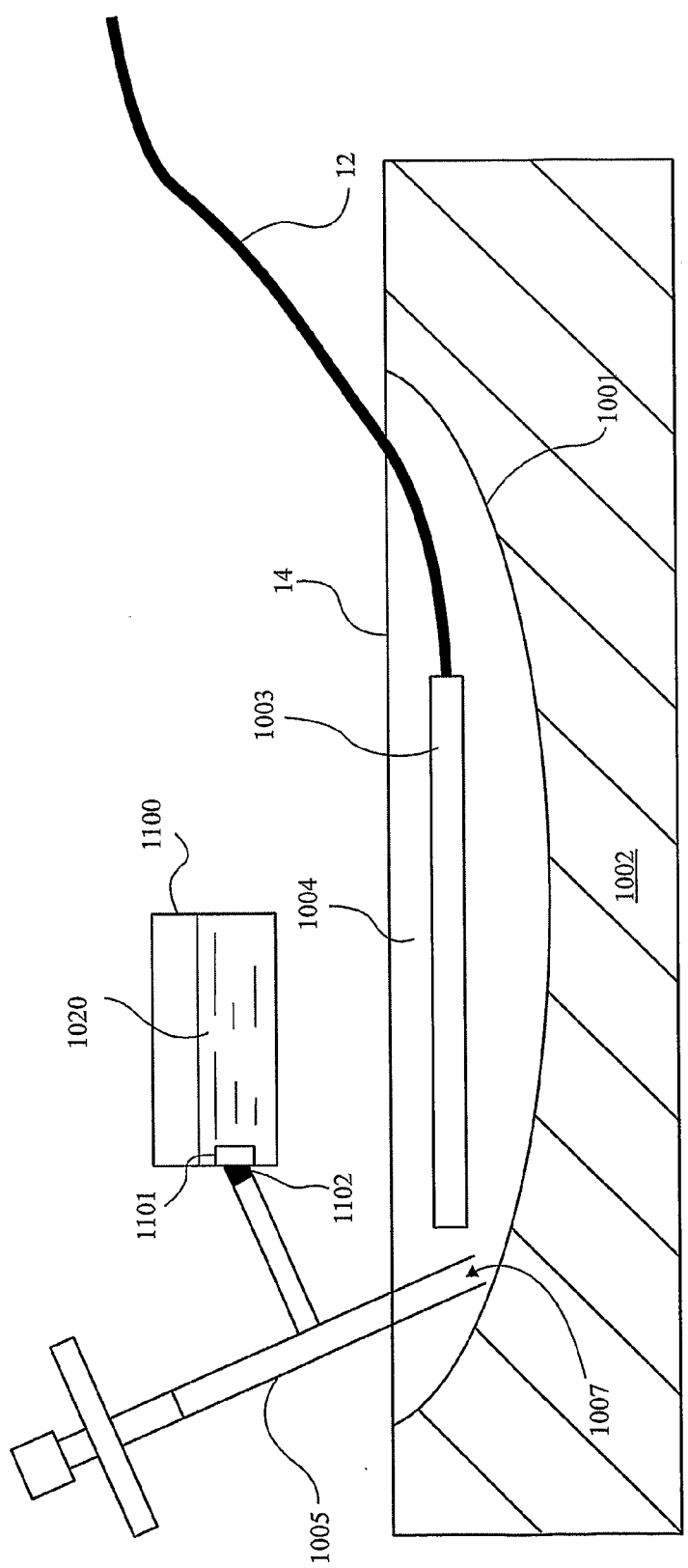
FIG. 11 illustrates an alternative wound site.

FIG. 11 illustrates an alternative embodiment of the present invention in which agent is introduced to a wound site from a reservoir 1100 containing the agent 1020 such as hydrating fluid. The agent 1020 can be released from the reservoir by a mechanical time release system 1101 arranged to periodically open a valve 1102 to release agent into the delivery tube. It will be appreciated by those skilled in the art that any other type of release system could be utilised for the reservoir 1010. For example but not exhaustively an electrical time release system could be utilised or the delivery tube 1005 could be connected to the container via an orifice or number of orifices each having a size predetermined so as to effectively drip agent into the wound bed region. Alternatively the valve may be kept open continuously.

Figure 12:
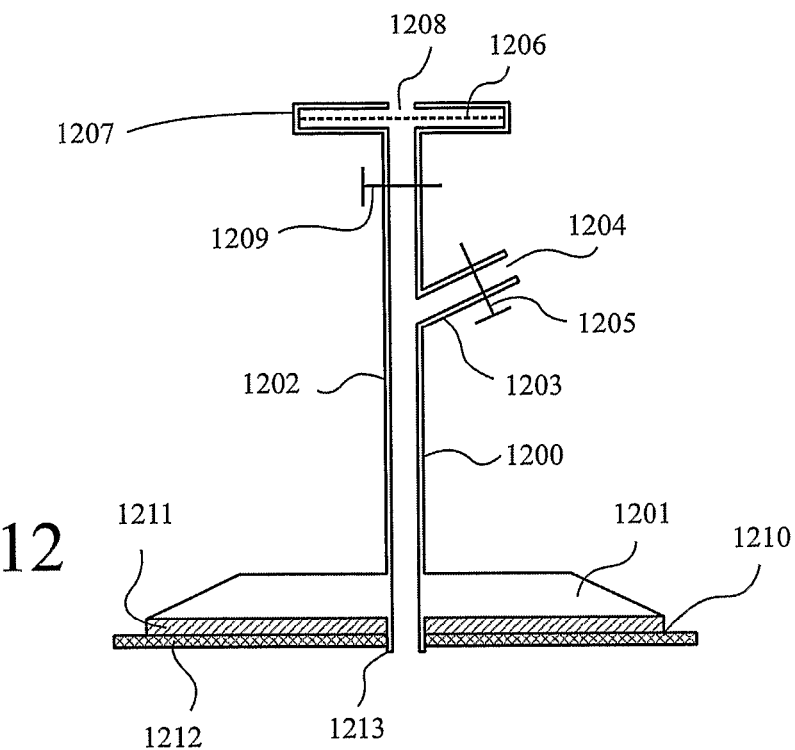
FIG. 12 illustrates how a delivery tube can be secured to a drape.

FIG. 12 illustrates an alternative embodiment of the present invention in which the delivery tube 1200 has a substantial disc like base section 1201 from which an upstanding tube 1202 extends. A side tube 1203 branches from the upstanding tube 1202 and has an agent inlet port 1204 controlled by an inlet valve 1205. It will be appreciated that agents can be introduced through the inlet port 1205 and inlet valve 1205 as described with the previous embodiments. The port 1204 may be protected by a septum not shown.

Likewise the upwardly extending delivery tube 1202 has a filter 1206 in an upper housing 1207. An opening 1208 allows air to enter the delivery tube where an air inlet valve 1209 is opened. A cap (not shown) may resealably seal 1208 in the delivery tube.

A lower surface 1210 of the delivery tube body 1201 carries an adhesive layer 1211 which is covered by protector paper 1212. The protector paper 1212 may be peeled away to reveal the adhesive as will be described herein below.

A penetrating portion 1213 of the delivery tube extends below a low surface of the disc like body 1201. The protrusion extends below this lower surface a sufficient distance so that penetration of a drape 14 can occur when the delivery tube is mounted on a sealed dressing.

The delivery tube shown in FIG. 12 provides a port which can be attached to a TNP dressing to provide access for agents to the wound. To attach the delivery tube the sealing layer of the TNP dressing, referred to here as a drape, is pierced to create a small hole of suitable size to accept the small protrusion of the conduit on the bottom face of the device. The protector layer 1212 is removed exposing the pressure sensitive adhesive layer. The device is then positioned such that the protrusion aligns with the pierced hole on the sealing means and a force applied to ensure that a good seal is made with the adhesive. The delivery tube may be made of any substantially rigid material but aptly a flexible polymeric material having a typical sure hardness 50-70A eg silicone, PVC, polyurethane or the like may be utilised. Furthermore the inlet 1204 may include a fitting to allow attachment of a device such as a syringe or reservoir as will be appreciated by those skilled in the art.

Figure 13:
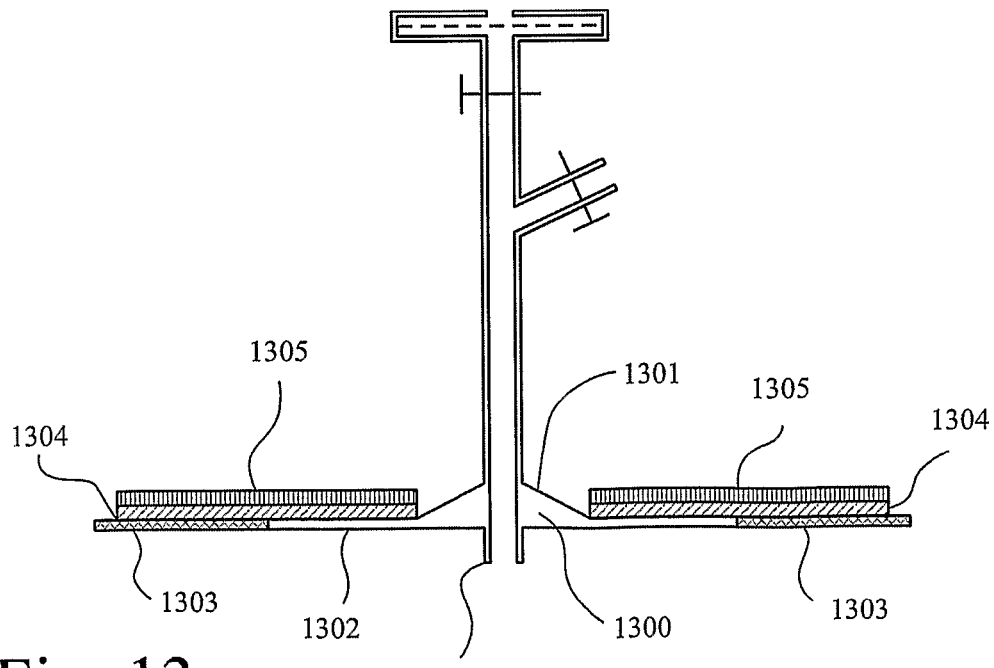
FIG. 13 illustrates a delivery tube securable between two drapes.

FIG. 13 illustrates an alternative embodiment of the present invention similar in many respects to that shown in FIG. 12 but in which the lower base portion 1300 includes a central substantially conical region 1301 which flares outwardly into a thinner disc-like region 1302. The thinness of the disc region 1302 means that the delivery tube can be secured between two sealing drapes of a dressing. The top drape is illustrated as drape 1305 which is a disc with central hole. To this end protector paper 1303 is provided to cover a lower surface of an adhesive layer 1304 which is adhered at an a proximal end to an upper surface to the disc-like portion 1302 of the delivery tube. An upper surface of the adhesive layer 1304 is covered by the drape 1305. Optionally the drape 1305 may have a further film (not shown) on top of it to strengthen the drape 1305 during assembly with the dressing. The film can be removed once the drape 1305 is firmly in place.

In order to secure the delivery tube to a dressing a small hole is first punctured in a lower sealing layer with the peeling paper being removed and then the delivery tube urged onto the lower drape so that the protrusion 1213 extends through the drape. The delivery tube is secured to the lower drape by the lower surface of the adhesive layer 1304.

Figure 14:
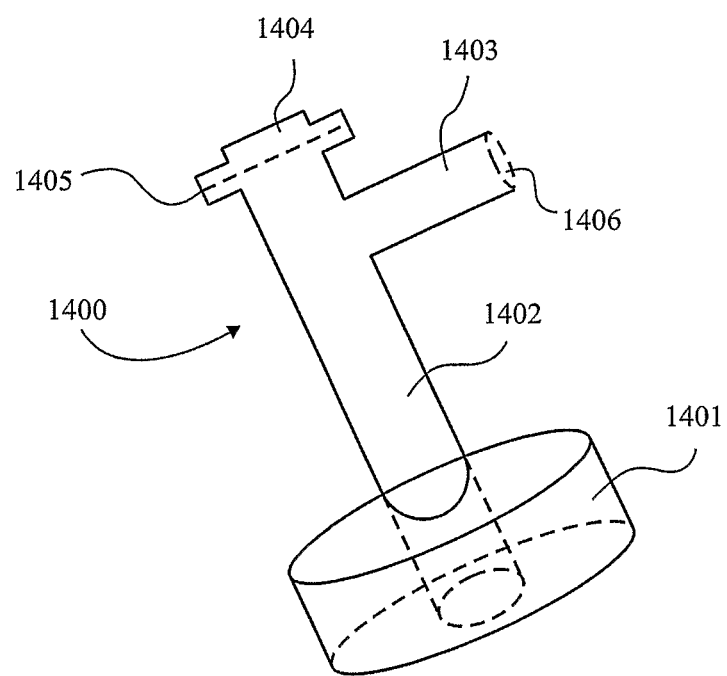
FIG. 14 illustrates a delivery tube.

FIG. 14 illustrates an alternative embodiment of the present invention in which a delivery tube 1400 has a lozenge shaped base section 1401 from which an upstanding tube 1402 extends. A side tube 1403, containing self sealing septum 1406, branches from the main tube 1402 and has an air inlet port 1404 and pathogen filter 1405. It will be appreciated that agents can be introduced through the septum 1406 by insertion of a hypodermic needle attached to a syringe preloaded with agent as described hereinabove with respect to the previous embodiments.

Figure 15:
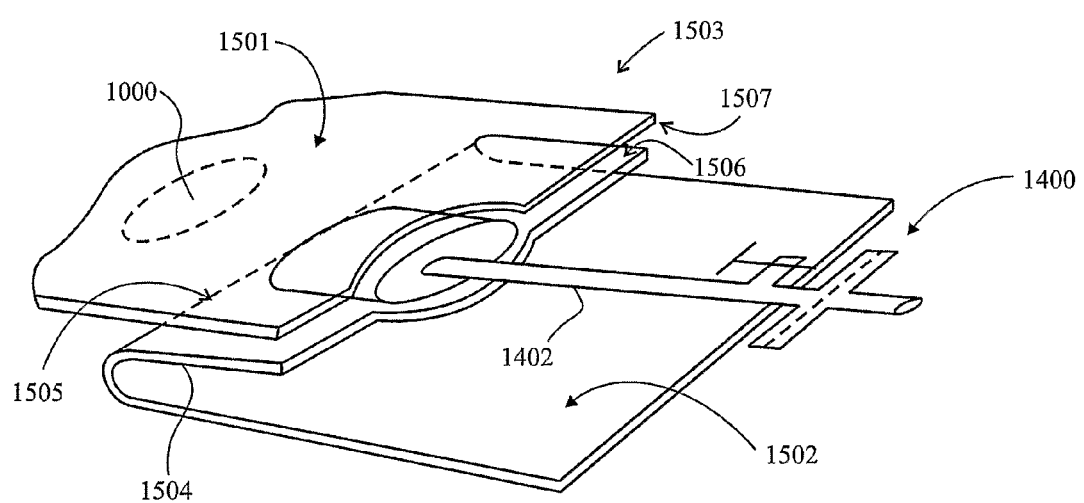
FIG. 15 illustrates the delivery tube shown in FIG. 14 located at a wound site.

FIG. 15 illustrates how the delivery tube 1400 illustrated in FIG. 14 can be located between a main drape 1501 and auxiliary drape 1502. As shown in FIG. 15 the delivery tube of this embodiment tends to lie sideways against a wound site. The use of the main drape 1501 and auxiliary drape 1502, which form a flap 1503, means that the delivery tube and portions of the main and auxiliary drape are movable. This makes the covering easier to put on and can be more comfortable to a patient. In addition, rather than the delivery tube extending outwardly from a wound site, the tube will lie substantially flat so that accidental disturbance of the delivery tube is kept to a minimum. This is particularly helpful when the delivery tube is used continuously as part of a drip process.

In order to locate the delivery tube 1400 at a wound site, the auxiliary drape 1502 is adhered to a target surface close to the wound site 1000. An end region 1504 of the auxiliary drape 1502 is folded back to form a fold line 1505. The upper surface 1506 is adhesive and the lozenge portion of the delivery tube 1402 can be adhered to this upper surface. Next the main drape 1501 is laid over the wound site covering the end region 1504 of the auxiliary drape. A lower surface 1507 of the main drape is adhesive so that the main drape and auxiliary drape can be pinched together around the lozenge base portion of the delivery tube 1400. As a result the flap 1503 is formed which can hingedly move around the hinge line 1505.

It will be appreciated that further passageways (not shown) can be formed through the lozenge section of the delivery tube 1400 to provide further input and output access to the wound site.

It will be appreciated by those skilled in the art that according to embodiments of the present invention rather than a syringe or reservoir being connected to the delivery tube the delivery tube may be connected directly to an outlet of a saline drip so that the wound bed may continuously be irrigated.

It will also be appreciated that from time to time using the syringe illustrated more clearly in FIG. 10 fluid may be drawn out from the wound bed region for sampling.

The provision of a passage through the drape 14 or under the drape means that from time to time fluid or dry agent may be introduced into a wound site without needing to move the dressing. This means that localised pain relief and/or antibiotics and/or wound irrigation may be introduced to a wound site without the need for regular changing of dressings. This can help prevent tissue infection, reduces cost, reduces pain to the patient and reduces the risk of patient to patient infection. It will also be appreciated that from time to time embodiments of the present invention allow wound fluid to be drawn out of the wound bed again without the need to disturb the drape 14 covering the wound dressing thus obviating certain disadvantages associated with prior art dressings.

Embodiments of the present invention enable agent to be introduced continuously or at predetermined time intervals into a wound site or for wound fluid to be drawn from the wound site either whilst topical negative pressure wound therapy continues or in such a way that TNP can be minimised Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith

What is claimed is:

1. Apparatus for delivering at least one agent to a wound site, comprising:
 a drape for covering a wound site;
 a negative pressure source;
 an aspiration conduit configured to fluidically connect the negative pressure source to the drape; and
 a delivery tube comprising a substantially T-shaped portion, comprising an outlet, an agent inlet port and a gas inlet port, wherein the gas inlet port is positioned upstream of the agent inlet port;
 wherein the gas inlet port further comprises an air filter; and
 wherein the drape is configured to maintain negative pressure provided from the negative pressure source at the wound site and the gas inlet port is configured to allow gas to flush the agent inlet port, flush the delivery tube, and to fill the wound when the wound site is maintained under negative pressure.

2. The apparatus according to claim 1, further comprising: an inlet valve downstream of the agent inlet port and a self sealing septum on the agent inlet port.

3. The apparatus according to claim 1, further comprising: a releasable cap connected to the gas inlet port.

4. The apparatus according to claim 1, further comprising: a syringe connectable to the agent inlet port.

5. The apparatus according to claim 1, further comprising: a reservoir having an outlet orifice connectable to the agent inlet port, wherein the reservoir comprises a mechanical or electrical time release system.

6. The apparatus according to claim 1, further comprising: the drape comprises a preformed aperture arranged to receive and seal against a portion of the delivery tube.

7. The apparatus according to claim 1, further comprising: a disc-like body portion extending outwardly around an outlet region of the delivery tube.

8. The apparatus according to claim 7, further comprising: a penetrating portion extending from a lower surface of the disk-like body portion.

9. The apparatus according to claim 1, further comprising: a drain locatable under the drape at the wound site.

10. The apparatus according to claim 9, wherein the aspiration conduit is connectable to the drain and the negative pressure source is an aspiration pump connectable to a proximal end of the aspiration conduit, and further comprising a filler for packing into the wound site.

11. The apparatus according to claim 1, wherein the substantially T-shaped portion of the delivery tube is a T-shaped portion.

* * * * *